(12) United States Patent
Shanmugam et al.

(10) Patent No.: US 7,447,345 B2
(45) Date of Patent: Nov. 4, 2008

(54) SYSTEM AND METHOD FOR GENERATING PET-CT IMAGES

(75) Inventors: Venkatesan Shanmugam, Milwaukee, WI (US); Mohammed Moin Hussaini, Baltimore, MD (US); Scott David Wollenweber, Advance, NC (US); Michael George Bonner, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 723 days.

(21) Appl. No.: 10/735,714

(22) Filed: Dec. 16, 2003

(65) Prior Publication Data

US 2005/0129295 A1 Jun. 16, 2005

(51) Int. Cl.
G06K 9/00 (2006.01)
A61B 5/05 (2006.01)
G01T 1/164 (2006.01)

(52) U.S. Cl. .................. 382/131; 600/427; 250/363.03

(58) Field of Classification Search ......... 382/128–131; 600/427, 431; 128/922; 250/363.03, 363.04
See application file for complete search history.

(56) References Cited

U.S. PATENT DOCUMENTS

| 5,241,181 | A | 8/1993 | Mertens et al. | |
|---|---|---|---|---|
| 5,272,343 | A | 12/1993 | Stearns | |
| 6,272,469 | B1 * | 8/2001 | Koritzinsky et al. | 705/2 |
| 6,462,342 | B1 | 10/2002 | Stearns | |
| 6,490,476 | B1 * | 12/2002 | Townsend et al. | 600/427 |
| 6,522,712 | B1 | 2/2003 | Yavuz et al. | |
| 6,915,004 | B2 * | 7/2005 | Newport et al. | 382/131 |
| 6,915,005 | B1 * | 7/2005 | Ruchala et al. | 382/131 |
| 6,937,750 | B2 * | 8/2005 | Natanzon et al. | 382/131 |
| 6,961,606 | B2 * | 11/2005 | DeSilets et al. | 600/415 |
| 7,046,831 | B2 * | 5/2006 | Ruchala et al. | 382/131 |
| 7,190,991 | B2 * | 3/2007 | Cable et al. | 600/407 |
| 2003/0161521 | A1 * | 8/2003 | Newport et al. | 382/131 |
| 2003/0190065 | A1 * | 10/2003 | Hamill et al. | 382/131 |
| 2004/0030246 | A1 * | 2/2004 | Townsend et al. | 600/427 |
| 2004/0167387 | A1 * | 8/2004 | Wollenweber et al. | 600/407 |

OTHER PUBLICATIONS

Samuel Matej, et al., "Performance of the Fourier Rebinning Algorithm for PET with Large Acceptance Angles," 43 Phys. Med. Biol. 787-795 (1998).

Eiichi Tanaka, Yuko Amo, "A Fourier Rebinning Algorithm Incorporating Spectral Transfer Efficiency for 3D Pet," 43 Phys. Med. Biol. 739-746 (1998).

T. Beyer, et al., "The Biograph: A Premium Dual-Modality PET/CT Tomograph for Clinical Oncology," 69 Electromedica, No. 2, 120-126 (2001).

* cited by examiner

*Primary Examiner*—Andrew W. Johns
*Assistant Examiner*—Andrae S Allison
(74) *Attorney, Agent, or Firm*—Hunton & Williams, LLP (57) ABSTRACT

The invention relates to a system and method for executing a scanning procedure comprising the steps of generating CT image data for a scan, generating CT attenuation correction data for the scan, acquiring a current frame of PET data for the scan in a 3D format, and simultaneously conducting the following steps: reconstructing at least a portion of a PET image for the current frame, including the step of overlapping a portion of the current frame with an adjacent frame, and acquiring at least a portion of a next frame of PET data.

20 Claims, 7 Drawing Sheets

SYSTEM AND METHOD FOR GENERATING PET-CT IMAGES

BACKGROUND

The present invention relates generally to imaging devices, and more particularly to a method and apparatus for simultaneously acquiring and processing image data.

Hospitals and other health care providers rely extensively on imaging devices such as computed tomography (CT) scanners, magnetic resonance imaging (MRI) scanners and positron emission tomography (PET) scanners for diagnostic purposes. These imaging devices provide high quality images of various bodily structures and functions. Each imaging device produces a different type of image based on the physics of the imaging process. For example, in a CT scanner, an x-ray source generates x-rays which propagate through the body and are detected by a detector on the other side of the body. The x-rays are attenuated to different degrees depending on what bodily structures they encounter, which results in an image showing the structural features of the body. CT scanners, however, are not particularly sensitive to biological processes and functions.

PET scanners, on the other hand, produce images which illustrate various biological process and functions. In a PET scan, the patient is initially injected with a radioactive substance known as a radiopharmaceutical. The radiopharmaceutical may be $^{18}$F-fluoro-2-deoxyglucose (FDG), for example, a type of sugar which includes radioactive fluorine. The radiopharmaceutical becomes involved in certain bodily processes and functions, and its radioactive nature enables the PET scanner to produce an image which illuminates those functions and processes. For example, when FDG is injected, it may be metabolized by cancer cells, allowing the PET scanner to create an image illuminating the cancerous region. PET scanners, however, do not generally provide structural details of the patient as well as other types of scanners such as CT and MRI scanners.

Recently PET-CT scanners have been introduced. A PET-CT scanner includes both a CT scanner and a PET scanner installed around a single patient bore. A PET-CT scanner creates a fused image which comprises a PET image spatially registered to a CT image. PET-CT scanners provide the advantage that the functional and biological features shown by the PET scan can be precisely located with respect to the structure illuminated by the CT scan. In a typical PET-CT scan, the patient first undergoes a CT scan, and then the patient undergoes a PET scan before exiting the scanner. After the CT and PET data have been acquired, the PET-CT scanner processes the data and generates a fused PET-CT image.

In PET-CT systems, the total effective examination time is the amount of time to acquire the PET and CT data, which may be significant, plus the amount of time to process the data. The data processing time after the CT and PET data have been acquired may also be significant, depending on the amount and type of data acquired. For PET-CT systems which perform 3D whole body (multiple frame) scans, the problem of long effective scan times can be exacerbated by the relatively long time it takes to process the 3D PET data.

The amount of time which a scanner takes to produce an image is very often an important consideration for hospitals and other health care providers in assessing the value of the scanner, particularly in the clinical environment. A scanner which can complete more scans per day is more valuable to the hospital than one which runs less efficiently, and therefore the hospital will be better able to justify the significant investment in a high-throughput scanner. In many existing PET-CT scanners, however, reconstruction times can be so long that 3D whole-body exams can become unacceptably long in clinical environments.

The present invention provides a method and apparatus for addressing these deficiencies.

SUMMARY

According to one embodiment, the invention relates to a method for executing a scanning procedure comprising the steps of generating CT image data for a scan; generating CT attenuation correction data for the scan; acquiring a current frame of PET data for the scan in a 3D format; and simultaneously conducting the following steps: reconstructing at least a portion of a PET image for the current frame, including the step of overlapping a portion of the current frame with an adjacent frame, and acquiring at least a portion of a next frame of PET data.

According to another embodiment, the invention relates to a PET-CT system comprising a CT detector; a PET detector; at least one memory; and at least one processor which is programmed to control a generation of CT image data for the scan, control a generation of CT attenuation correction data for the scan, control an acquisition of a current frame of PET data for the scan in a 3D format, and control a simultaneous execution of (a) a reconstruction of at least a portion of a PET image for the current frame, including overlapping a portion of the current frame with an adjacent frame, and (b) an acquisition of at least a portion of a next frame of PET data.

DETAILED DESCRIPTION

Figure 1:
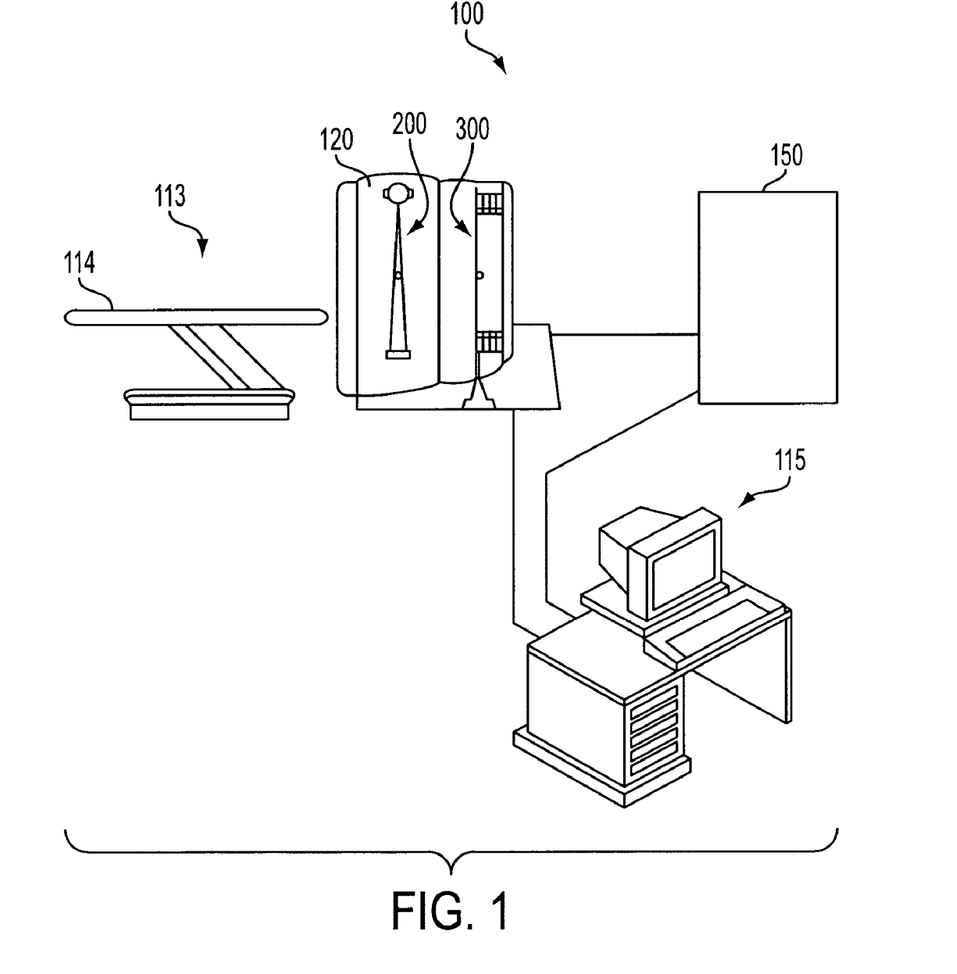
FIG. 1 is a drawing of a PET-CT imaging system according an exemplary embodiment of the invention.

FIG. 1 is a drawing of a PET-CT scanner 100 according to an exemplary embodiment of the invention. The PET-CT scanner 100 includes a CT system 200 and a PET system 300 mounted around a bore in a housing 120. The PET-CT scanner 100 also includes a patient table 113, a table bed 114, a processing unit 150, and a control station 115. A patient table controller (not shown) moves the table bed 114 into the bore in response to commands received from the control station 115. The control station 115 typically includes a display and one or more input devices such as a keyboard or a mouse. Through the keyboard and associated input devices, the operator can control the operation of the PET-CT scanner 100 and the display of the resulting image on the display.

The processing unit 150 includes one or more processors, one or more memories, and associated electronics for image processing. The processing unit 150 processes the data acquired by the CT system 200 and the PET system 300 under control of the operator operating the control station 115. The operation of the CT system 200 will be described with reference to FIG. 2. The operation of the PET system 300 will be described with reference to FIGS. 3-4.

Figure 2:
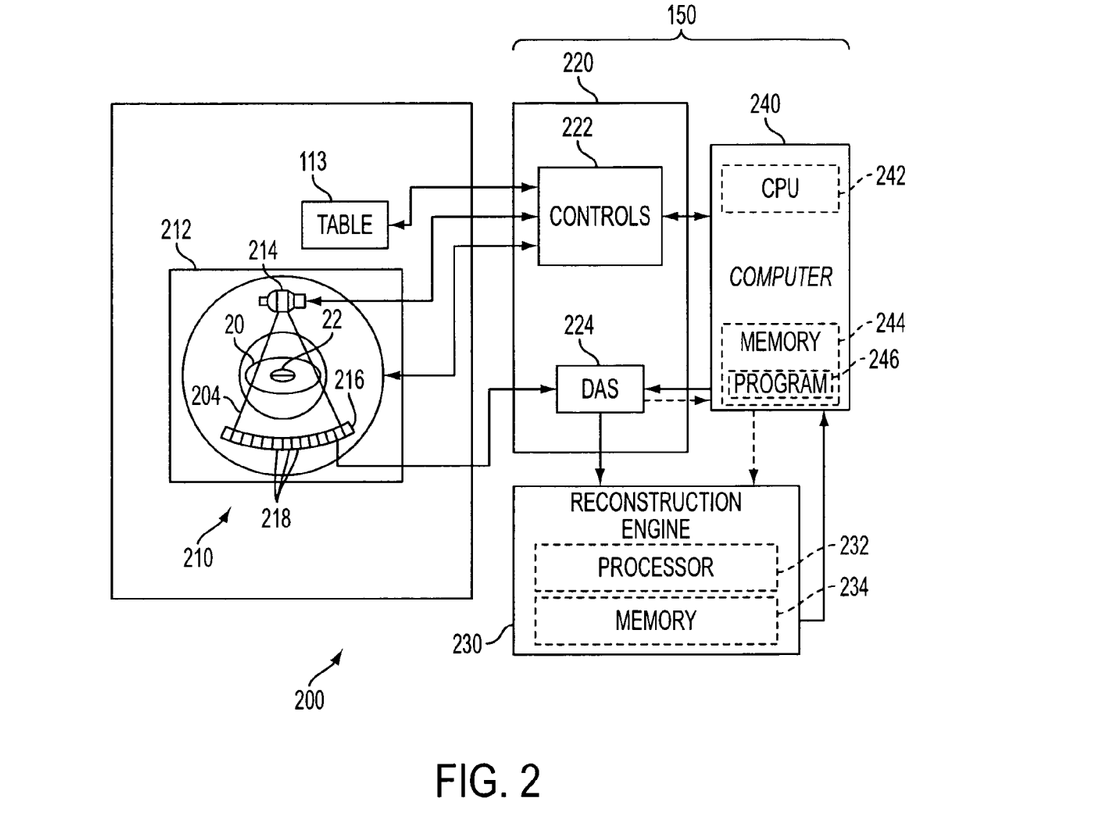
FIG. 2 is a diagram of the CT system of FIG. 1 according to an exemplary embodiment of the invention.

FIG. 2 is a schematic illustration showing the major components of the CT system 200 of FIG. 1. The components of the CT system 200 are typically housed both in the housing 120 supporting the CT detector 200 and in the processing unit 150 shown in FIG. 1. A subject 20 for imaging is typically a human patient who may be undergoing diagnostic assessment for coronary artery disease or other disease processes. As is well known, x-ray tomographic imaging with such a CT system 200 is typically carried out by illuminating the subject 20 with an x-ray beam 204 substantially transverse to an axis through the subject 20. Typically the axis is centered on an object 22 of interest, such as an organ or other tissue structure. The subject 20 may be located on the table bed 114 shown in FIG. 1 that translates along the direction of the axis, thereby enabling illumination of a volumetric portion of the subject 20 by the x-ray beam 204.

The CT system 200 comprises a source-detector assembly, which in an exemplary embodiment may comprise a gantry 212 rotatable about the axis. An x-ray source 214, such as an x-ray tube, may be mounted on the gantry 212 and may rotate with rotation of the gantry 212. The x-ray source 214, which may comprise a collimating element (not shown), projects the beam 204 of x-rays toward a detector array 216 disposed opposite the source 214 relative to the gantry 212.

The detector array 216 is typically comprised of numerous individual detector elements 218. Detector elements 218 together provide information regarding the internal structures of the subject 20, such as the object 22. In the typical case, each detector element 218 generates an electrical signal indicating the intensity of a portion of the x-ray beam 204 impinging thereupon.

The signals from detector elements 218 may indicate a degree of attenuation of the beam 204 as the x-rays traverse the material or substance of the subject 20. Typically the source 214 is rotated around the subject 20 to execute a scan operation whereby the CT system 200 acquires x-ray data. The gantry 212, with source 214 attached to a side portion thereof, typically rotates about the axis of the subject 20 to acquire x-ray data from numerous different illumination angles or "view angles."

The rotation operation for the source 214 is controlled by a control/interface system 220. The control/interface system 220 may comprise a server computer residing in the processing unit 150 and the operator may interact with the control/interface system 220 by means of the control station 115 and/or other input devices. The control/interface system 220 provides control for positioning of the gantry 212 relative to the subject 20, such as controlling speed of rotation about the axis and control of relative positions of the table 113 and the gantry 212. The controls section 222 also typically provides control over x-ray generation (power and timing) of the source 214. The control/interface system 220 also includes a data acquisition system (DAS) 224 that samples the detector signals generated from the detector elements 218 and converts the sampled signals into digital data for further processing.

A reconstruction engine 230, which may also be housed in the processing unit 150, receives the sampled and digitized data (sometimes referred to as "projection data") from the DAS 224 and performs image reconstruction to generate CT images. The reconstruction engine 230 may comprise a separate processor 232 and memory 234, for example. Various algorithms are well known in the art for reconstructing a CT image from projection data comprising a plurality of projection views. Typically, the CT image is generated in a format compatible with the DICOM (Digital Imaging and Communications in Medicine) standard. The DICOM standard specifies the network protocol by which two DICOM-compatible systems communicate.

The reconstruction engine 230 may send the reconstructed CT image to, for example, a system management computer 240, which may also reside in the processing unit 150, for storage or further processing. The computer 240 typically comprises a CPU (a processor) 242 and a memory 244.

Figure 3:
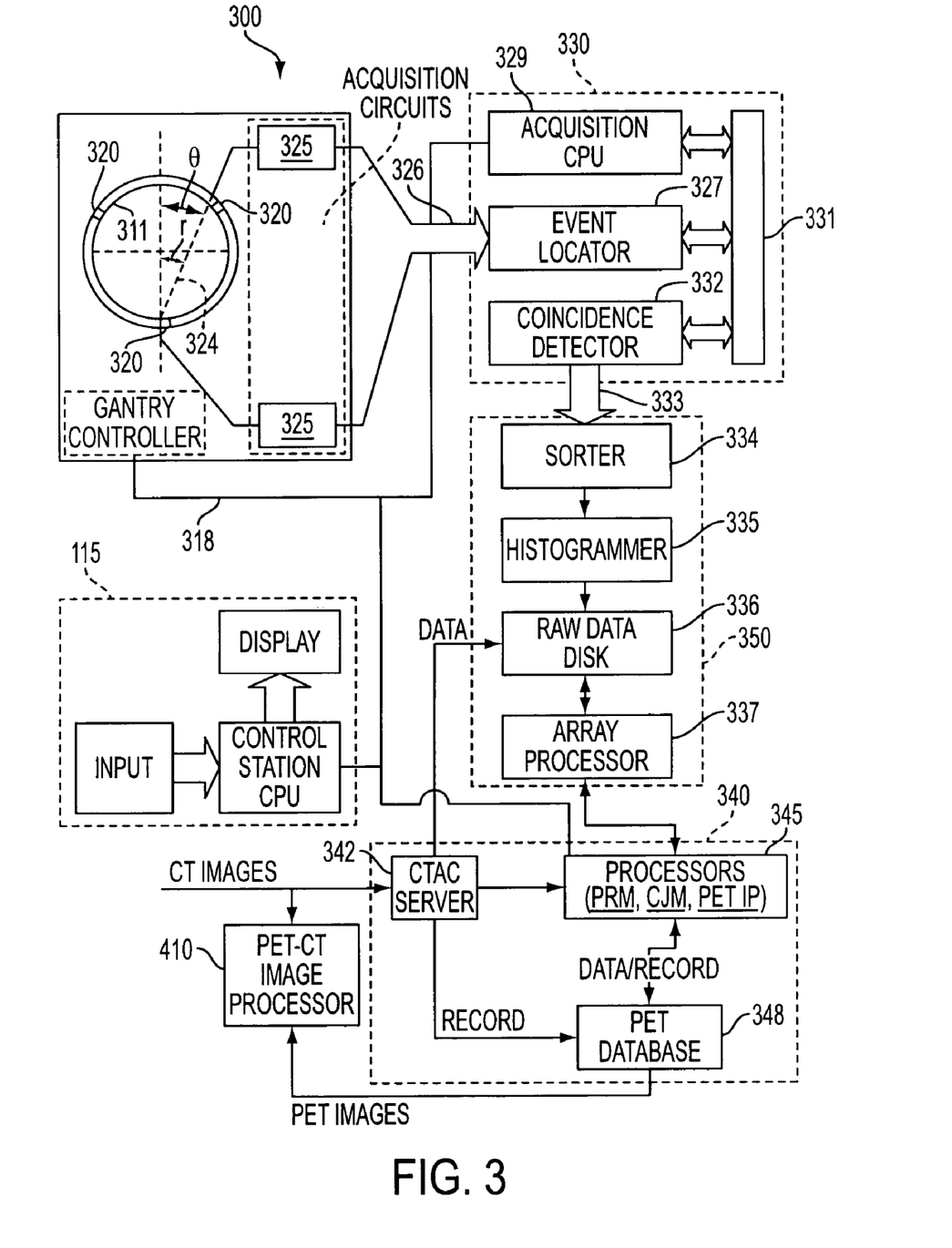
FIG. 3 is a diagram of the PET system of FIG. 1 according to an exemplary embodiment of the invention.

FIG. 3 is a schematic illustration of the PET system 300 of FIG. 1. The PET system 300 includes detector ring assembly 311 disposed about the patient bore. The detector ring assembly 311 is made up of multiple detector rings that are spaced along the central axis to form a cylindrical detector ring assembly. Each detector ring of the detector ring assembly 311 is comprised of detector modules 320. Each detector module 320 typically comprises an array (e.g., a 6×6 array) of individual detector crystals which may be formed of bismuth germanate (BGO), for example. The detector crystals detect gamma rays emitted from the patient and in response produce photons. Typically the array of detector crystals are disposed in front of four photomultiplier tubes (PMTs). The PMTs produce analog signals when a scintillation event occurs at one of the detector crystals, i.e., when a gamma ray emitted from the patient is received by one of the detector crystals. A set of acquisition circuits 325 is mounted within the housing 120 to receive these signals and produce digital signals indicating the event coordinates (i.e., the location of the detected gamma ray) and the total energy of the gamma ray. These are sent through a cable 326 to an event locator circuit 327. Each acquisition circuit 325 also produces an event detection pulse (EDP) which indicates the time the scintillation event took place.

The event locator circuits 327 form part of a data acquisition processor 330 which periodically samples the signals produced by the acquisition circuits 325. The processor 330 has an acquisition CPU 329 which controls communications on the local area network 318 and a backplane bus 331. The event locator circuits 327 assemble the information regarding each valid event into a set of digital numbers that indicate precisely when the event took place and the position of the detector crystal which detected the event. This event data packet is conveyed to a coincidence detector 332 which is also part of the data acquisition processor 330.

The coincidence detector 332 accepts the event data packets from the event locator circuits 327 and determines if any two of them are in coincidence. Coincidence is determined by a number of factors. First, the time markers in each event data packet must be within a certain time period of each other, e.g., 12.5 nanoseconds, and second, the locations indicated by the two event data packets must lie on a straight line which passes through the field of view (FOV) in the patient bore. For a detailed description of the coincidence detector 332, reference is made to U.S. Pat. No. 5,241,181 entitled "Coincidence Detector For A PET Scanner." Coincidence event pairs are located and recorded as a coincidence data packet that is conveyed through a link 333 to a storage subsystem 350. In the storage subsystem 350, a sorter 334 may use a lookup table to sort the coincidence events in a 3D projection plane format. For a detailed description of the sorter 334, reference is made to U.S. Pat. No. 5,272,343 entitled "Sorter For Coincidence timing Calibration In A PET Scanner." The detected events may be stored in a dynamic histogram memory (histogrammer 335) where the events are ordered by radius and projection angles. The PET data for a particular frame may be written to a raw data disk 336.

As is known in the art (see, e.g., U.S. Pat. No. 6,462,342), PET scanners can be configured to operate in two different modes, 2D and 3D, related to the annihilation events which can be observed by a particular detector ring. In 2D (multiplanar) PET scanners, each detector ring is configured to only detect annihilations occurring within the plane of that respective detector ring or an immediately adjacent detector ring, and not to detect annihilations occurring at other positions within the PET scanner (i.e., annihilations occurring within the other detector rings of the PET scanner). Such multiplanar data can be organized as a set of two-dimensional sinograms. In 3D (volumetric) PET scanners, the detectors of each detector ring can receive photons from a wider range of angles than in 2D scanners.

Figure 4:
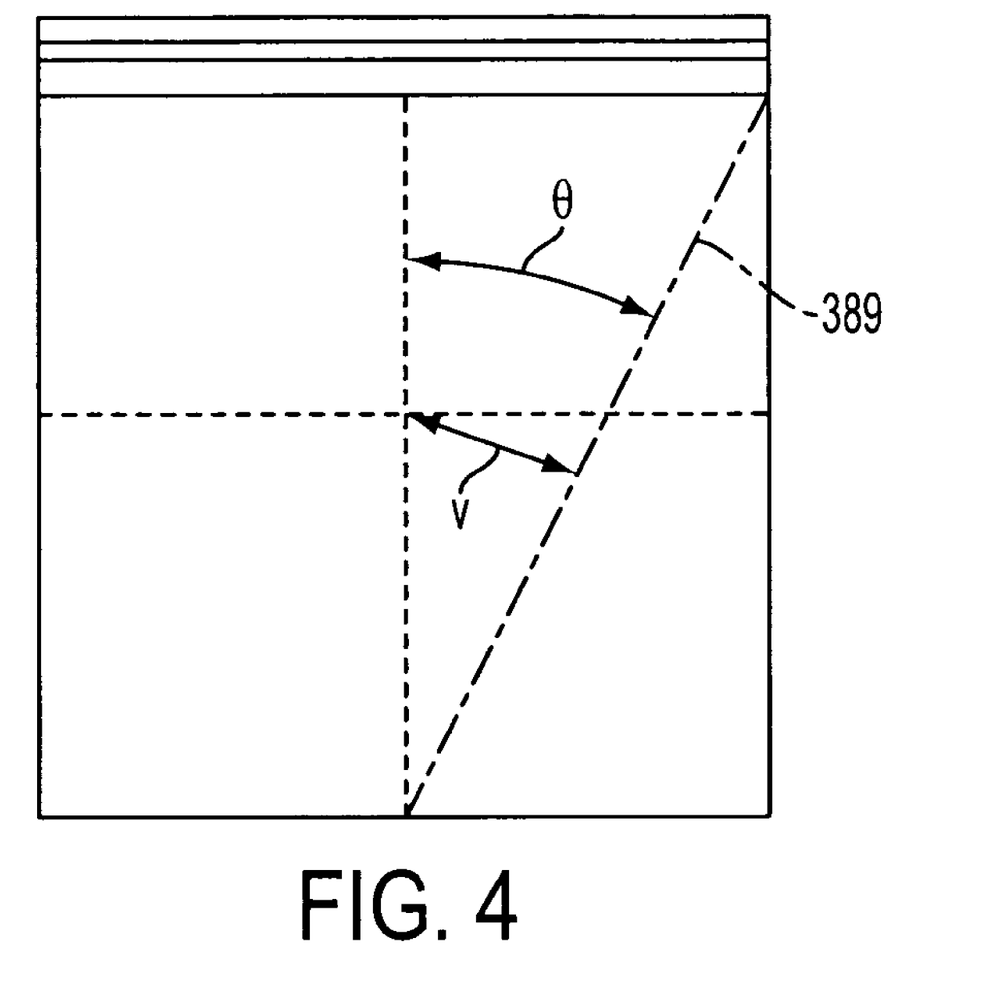
FIG. 4 is a drawing of variables used in the projection plane data format according to an exemplary embodiment of the invention.

3D PET scanners determine the existence of, and process information related to, coincidence events that occur not merely between pairs of detectors positioned on a single (or immediately adjacent) detector ring, but also between pairs of detectors positioned on detector rings that are spaced more than one ring apart. In 3D PET scanners, each pair of event data packets that is identified by the coincidence detector 332 is typically described in a projection plane format using four variables r, v, $\theta$ and $\phi$, i.e., according to the form $p_{\theta,\phi}(r,v)$, as shown in FIGS. 3 and 4. In particular, the variables r and $\phi$ identify a plane 324 that is parallel to the central axis of the PET scanner, with $\phi$ specifying the angular direction of the plane with respect to a reference plane and r specifying the distance of the central axis from the plane as measured perpendicular to the plane. As further shown in FIG. 4, the variables v and $\theta$ further identify a particular line 389 within that plane 324, with $\theta$ specifying the angular direction of the line within the plane, relative to a reference line within the plane, and v specifying the distance of the central point from the line as measured perpendicular to the line.

3D PET scanners allow for increased sensitivity relative to 2D multiplanar scanners, since more coincidence events can be recorded. However, 3D PET scanners also admit more scattered and random coincidence events to the data set from which the image is reconstructed than 2D multiplanar scanners. 3D PET scanners also produce more data, which can significantly increase the image processing time.

According to an exemplary embodiment of the invention, the PET system 300 operates as a 3D system. The sorter 334 counts all events occurring along each projection ray (r, v, $\theta$ and $\phi$), and stores that information in the projection plane format.

The PET system 300, as shown in FIG. 3, may include one or more additional processors 345 such as, for example, a prospective reconstruction manager (PRM), a compute job manager (CJM), and a PET image processor (PET IP). The processors 345 may interact with an array processor 337 in the storage subsystem 350 to process the projection plane format PET data into attenuation corrected PET images, as will be described below in more detail.

FIG. 3 also shows a computed tomography attenuation correction (CTAC) server 342. The CTAC server 342 may execute an independent process that runs in the processing unit 150. The CTAC process may receive CT image data from the CT system 200 and convert that CT image data into CTAC data. For example, the CTAC process may receive a request from the CT system and perform a bi-linear or other algorithm to convert the data from CT image units (Hu) to a PET 511 keV attenuation coefficient (cm$^{-1}$), which produces the CTAC correction for PET data from the CT images. Once the CT images are converted to CTAC data, the CTAC server 342 may write the CTAC data to the raw data disk 336 in the storage subsystem 350. At the same time, a record may be transmitted to the PET database 348 to create a data link (CTAC record) to the CTAC data.

FIG. 3 also shows a PET-CT image processor 410 which receives CT images and PET images. The CT images and the PET images are spatially registered to each other because the patient undergoes both scans while remaining in the same position on the table bed 114. The PET-CT image processor 410 generates a fused PET-CT image using the input CT and PET images.

Of course, the arrangement shown in FIGS. 1-4 is merely an example. The PET-CT scanner 100, for example, may include a different configuration or number of processors and memories and other hardware, to perform the various functions, and these components may be located at other locations such as the control station 115, or at another server or processing unit. The system 100 can be configured as desired, as will be appreciated by those skilled in the art.

Figure 5:
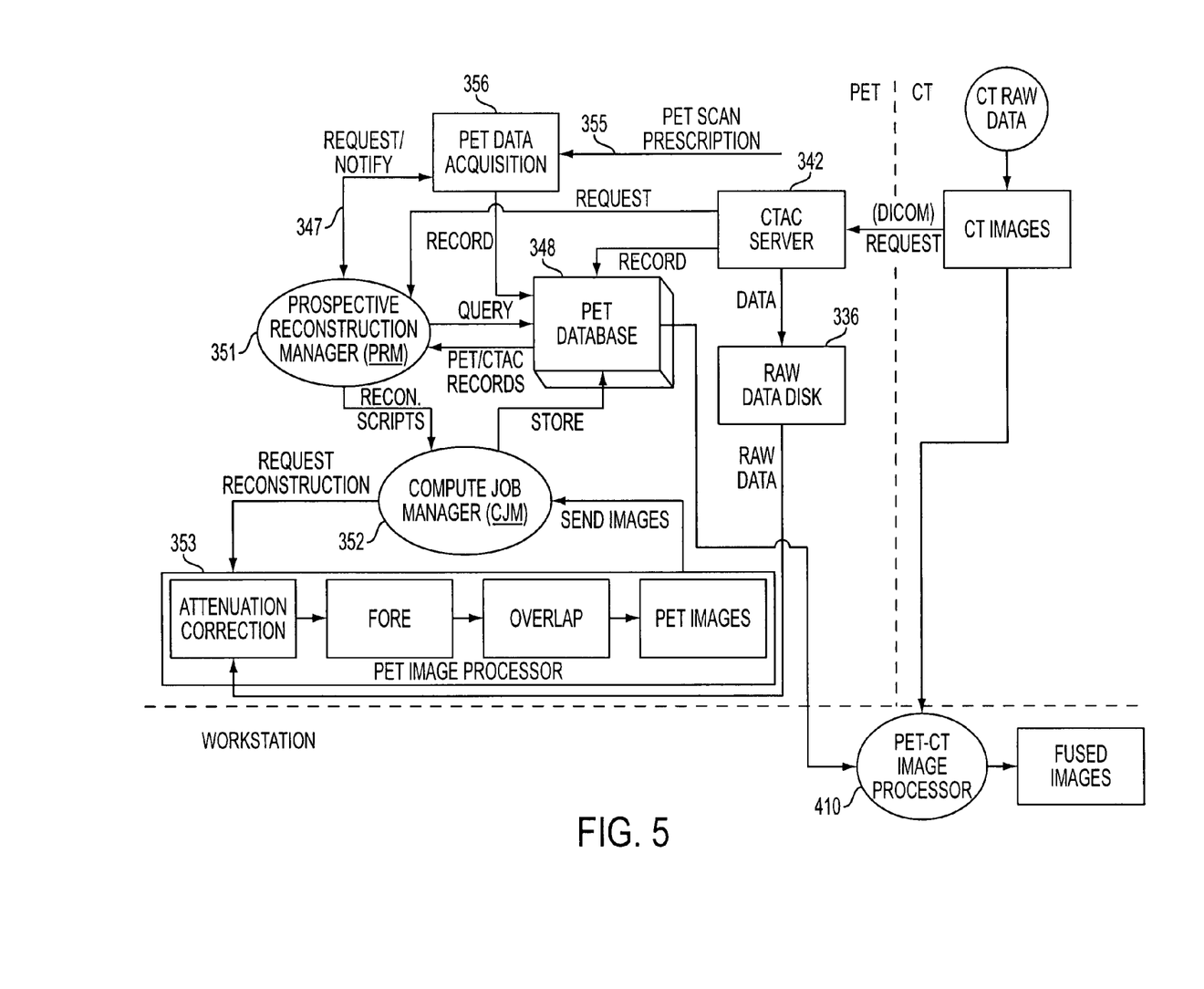
FIG. 5 is a diagram showing the flow of image data in a PET-CT scanner according to an exemplary embodiment of the invention.
Figure 6:
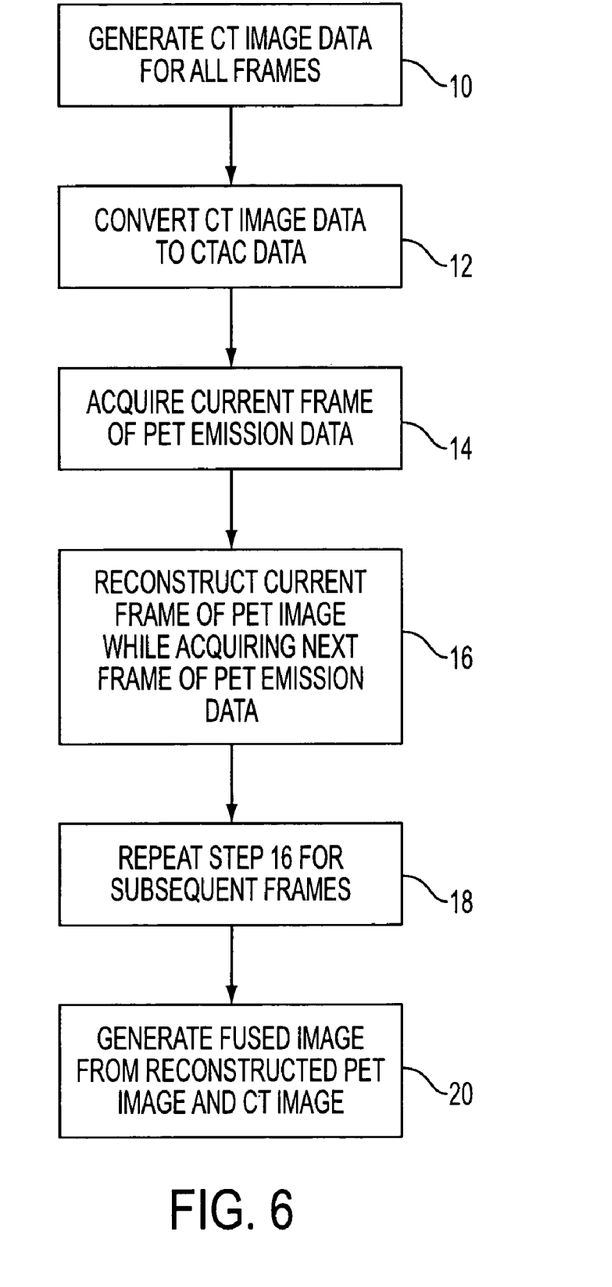
FIG. 6 is a flow chart showing a method of simultaneously acquiring and processing PET data according to an exemplary embodiment of the invention.

The operation of the PET-CT scanner 100 will now be described according to an exemplary embodiment of the invention with reference to FIGS. 5 and 6. FIG. 5 is a diagram illustrating the flow of image data according to an exemplary embodiment of the invention. FIG. 6 is a flow chart describing the simultaneous acquisition of PET data and reconstruction of a PET image according to an exemplary embodiment of the invention.

Referring to FIG. 6, the process begins at step 10, in which the CT system 200 generates CT image data. In particular, the data acquisition system (DAS) 224 (see FIG. 2) of the CT system 200 is operated to acquire CT data, as described above, and the reconstruction engine 230 of the CT system 200 generates CT images for all frames prescribed by the operator of the scanner 100. At the conclusion of step 10, all of the CT images for the scan are stored in the memory 234 of the reconstruction engine 230 or in the memory 244 of the system management computer 240. FIG. 5 shows the generation of CT images from CT data on the right hand side of the diagram.

In step 12, the CT images are sent to the CTAC server 342 which converts the CT images into CTAC data. Based on a bi-linear function, for example, the CT data in CT image units may be converted to PET attenuation coefficients (CTAC data). The CTAC data is used for attenuation correction of the PET data during the PET image reconstruction process. As shown in FIG. 5, the CTAC data are then transmitted by the CTAC server 342 to the raw data disk 336 for storage while a record is transmitted to create a data link (CTAC record) in the PET database 348.

In step 14, the PET system 300 acquires a first frame of PET data, as described above with respect to FIG. 3. The detector crystals of the PET system 300 detect gamma rays emitted from the patient, and the acquisition circuits 325, event locator circuits 327, and coincidence detector 332 together record coincidence events which are the basis of the PET data. The sorter 334 uses a lookup table to sort the coincidence events in a 3D projection plane format. The detected events are stored in the histogrammer 335 where the events are ordered by radius and projection angles. At the conclusion of step 14, the PET data for a particular frame are written to the raw data disk 336 and a data link (PET record) is created and stored in PET database 348.

According to one aspect of the invention, the system 100 can be programmed such that a CT prescription by the operator automatically sets up and specifies a corresponding 3D PET prescription and protocol. This functionality is shown in FIG. 5 by the line 355 which represents the prescription of a PET scan data acquisition phase based on the corresponding CT scan.

In step 16, the first frame of PET data is reconstructed into a PET image while a second frame of PET data is being acquired. This step can provide the significant advantage that reconstruction of the PET image can begin immediately after the first frame of PET data is acquired, rather than waiting until all the PET data has been acquired. In a conventional PET-CT system, in the case of a scan comprising multiple frames of 3D PET data, the time typically required to reconstruct the PET image once the PET data and CTAC data have been acquired can be significant, e.g., 3-4 minutes per frame. In a conventional PET-CT system, for a scan consisting of 7 frames, the image reconstruction time at the end of all data acquisition would be 21-28 minutes, which may significantly affect the throughput of the PET-CT system. According to exemplary embodiments of the invention, the only image reconstruction which takes place at the conclusion of PET data acquisition is the image reconstruction for the final frame of PET data, since the other PET data has already been reconstructed. The data acquisition process for the CT and PET data according to an exemplary embodiment of the invention can proceed sequentially without any significant interruptions, and the subsequent PET image reconstruction of one final frame of PET data can occur immediately after the conclusion of the PET data acquisition. With 3D PET data, the image processing for the final frame of PET data may take approximately 3-4 minutes, for example. The actual processing time may also depend on the specific configurations of the system. A typical 3D exam (including acquisition and reconstruction) using 7 bed positions, at 3 minutes per bed position scan time, used to take a total of 42-49 minutes. However, it may take only 21-24 minutes using a PET-CT system according to exemplary embodiments of the invention. Of course, these durations are merely examples.

As shown in FIG. 5, the image processing is controlled by, among other things, a prospective reconstruction manager (PRM) 351. The PRM, which may comprise a software routine running on a server computer, coordinates the prescriptions of recently acquired frames of PET data with the availability of CTAC data sets produced by the CTAC server 342. The PRM 351 checks the PET database 348 for a corresponding CTAC record before submitting a frame of PET data to the PET image processor 353 for reconstruction.

During the acquisition phase of a frame of PET data, notifications are sent by the PET data acquisition routine 356 to the PRM 351 via line 347 when the acquisition of a frame of PET data has been completed. In response to the notification, the PRM 351 sends a query to the PET database 348 inquiring as to whether the CTAC data corresponding to that frame is available. The PET database 348 responds by providing a CTAC record, if available, to the PRM 351. The PRM 351 then sends the CTAC record, the PET record, and reconstruction instructions, all included in one or more reconstruction scripts, to the Compute Job Manager (CJM) 352. Once it completes processing of each frame of CT image data, CTAC server 342 may also send requests to PRM 351, which may be caused to query the PET database 348 for corresponding PET emission data and CTAC data.

The CJM 352, which may comprise a software routine running on a server computer, formulates a reconstruction request and sends it with the CTAC record and the PET record to the PET image processor 353 for reconstruction. The reconstruction request formulated by the CJM 352 may specify, among other things, file names for all the relevant files containing image data, corresponding frame numbers for the PET and CTAC data, slice numbers to be overlapped, and whether to read a file from a previous frame for overlapping or whether to write a file for overlapping with a subsequent frame. The CJM 352 may create an overlap map comprising a list of structures where each node includes a corresponding slice's references to the slice and frame with which it overlaps. The overlap map stores pointers to both previous and next frames. This allows the CJM 352 to prescribe the handling of front and rear overlap regions within the processing of a single frame.

Figure 7:
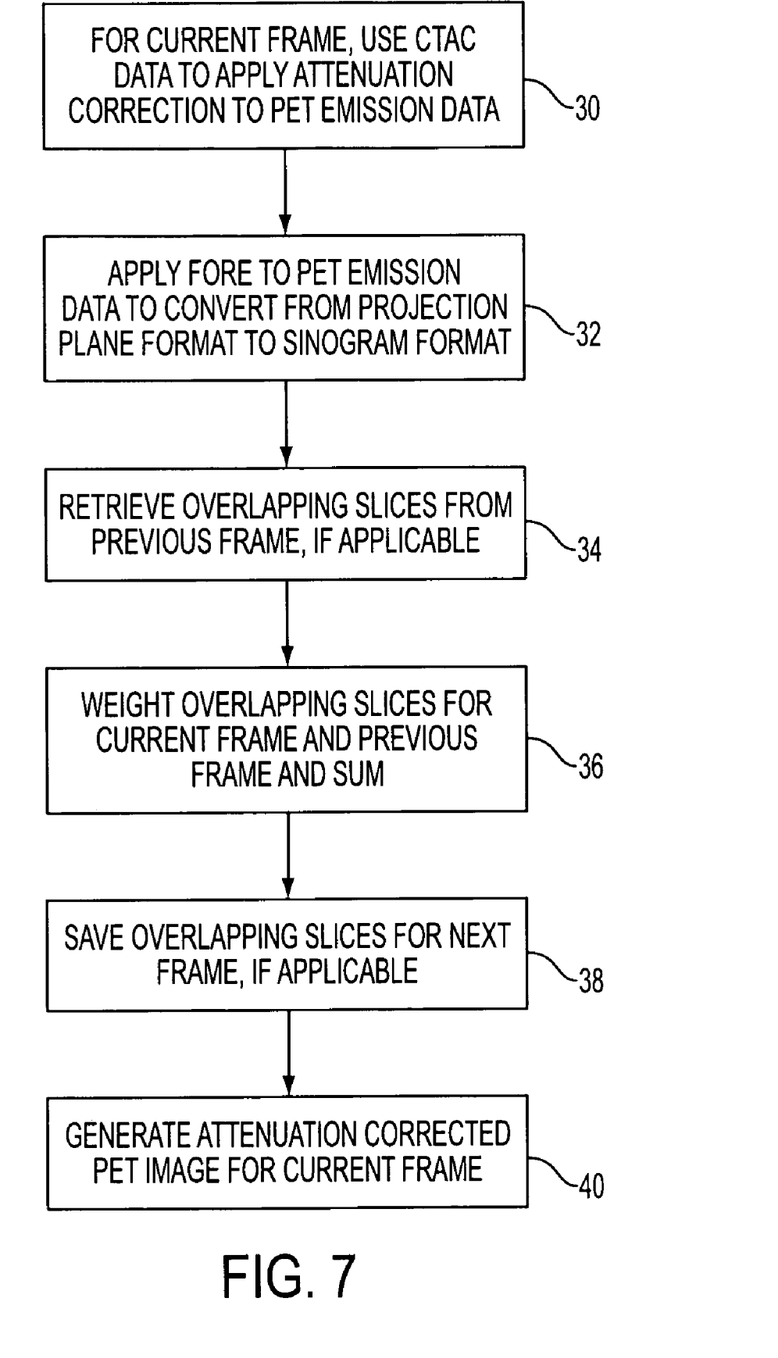
FIG. 7 is a flow chart showing steps involved in reconstructing a PET image from PET data and CT attenuation correction data according to an exemplary embodiment of the invention.

The PET image processor 353 performs a number of operations on the PET data, including attenuation correction, Fourier rebinning (FORE), overlapping adjacent frames, and PET image generation, as will be described further below with reference to FIG. 7.

At the conclusion of step 16, a PET image has been reconstructed for the current frame and is stored in the PET database 348. The reconstruction of the PET image for the current frame occurs while the PET system 300 is acquiring PET data for the next frame. This parallel processing (PET data acquisition of next frame with PET image reconstruction of current frame) can significantly reduce the total PET-CT exam time.

Step 18 entails repeating step 16 (reconstructing current frame of PET image while acquiring next frame of PET data) for at least one and typically a plurality or all subsequent frames in the scan until all the prescribed data has been acquired and reconstructed. At the conclusion of step 18, all of the PET images will be stored in the PET database 348.

In step 20, the CT images and the PET images are sent to the PET-CT image processor 410 which generates a fused PET-CT image. The two image data sets (PET and CT) used to construct the fused PET-CT image are spatially registered to each other, because the patient has undergone both scans while remaining in the same position on the table bed 114. The fused PET-CT image shows anatomical structures and locations from CT along with the metabolic activity from PET. The PET-CT image processor 410 is typically part of a workstation used for examining images. According to one embodiment, an eNTegra™ workstation available from GE Medical Systems can be used. The eNTegra™ workstation has, among other things, an image fusion capability, which employs registration (matrix transformation) of CT's coordinate system to the PET's coordinate system.

The PET image reconstruction process will now be described in more detail with reference to the flow chart of FIG. 7. Initially, the PET image processor 353 receives a reconstruction request from the CJM 352. In step 30, the PET image processor 353 retrieves the CTAC data and PET data from raw data disk 336 based on the CTAC record and PET record received from the CJM 352. The CTAC data are used to apply an attenuation correction to the PET data for the corresponding frame. Attenuation correction is the multiplicative process of correcting the native PET emission data for losses of coincidence events due to one or both of the gamma rays interacting in the object being imaged.

Next, in step 32, a Fourier rebinning process (FORE) is applied to the attenuation corrected PET data to convert it directly to sinogram format. The PET image processor 353 converts the attenuation corrected PET data, which is in a 3D projection plane format $(p_{\theta,\phi}(r,v))$ into a 2D sinogram array $(p_z(r,\phi))$ which is stored in a memory (not shown) associated with the PET image processor 353. Conversion of the PET data to the sinogram format with the FORE process provides the advantage that adjacent frames of PET data can be overlapped slice by slice to improve accuracy in the resulting image. In addition, the image reconstruction can be completed in less time using input data in sinogram format as opposed to using input data in projection plane format. The process of converting PET data in projection plane format directly into the two-dimensional sinogram format is known in the art and described, for example, in U.S. Pat. No. 6,462,342. According to the FORE process, an angular portion of the data obtained in the projection plane format can be decimated in a particular manner so that portions of the total amount of data can be read into memory, sorted into sinogram fragments, operated on by way of reduced-length two-dimensional discrete Fourier transforms, and then added together to obtain a set of two dimensional sinograms. The two-dimensional sinograms obtained from the operation are the same set of sinograms as would be obtained by resorting the data from the projection plane format into the cross-plane sinogram format and then performing the FORE algorithm upon that cross-plane sinogram data. See also E. Tanaka and Y. Amo, "A Fourier Rebinning Algorithm Incorporating Spectral Transfer Efficiency for 3D PET," 43 Phys. Med. Biol. 739-746 (1998); S Matej et al., "Performance of the Fourier Rebinning Algorithm for PET with Large Acceptance Angles," 43 Phys. Med. Biol. 787-795 (1998).

In steps 34, 36, and 38, the PET data which has been converted to sinogram format is overlapped with adjacent frames. The overlap function can enhance the accuracy of the resulting PET images, for example by reducing or eliminating the detector sensitivity artifacts associated with 3D scans. One typical objective of whole-body PET scans is to produce images of uniform quality both across the imaging plane and in the axial direction (along the sections of the object imaged). Overlapping is advantageous since it reduces noise caused by lost sensitivity in the end slices. The typically high noise in the end slices is reduced by weighted averaging of the low count (low-sensitivity) slices included in the overlap.

In general, the overlap process entails defining an overlap region between two adjacent frames of PET data in terms of a number of overlapping slices. Typically, a full frame of PET data comprises 35 slices, and the overlap region comprises about 5-7 slices. Once the overlapping slices are defined, the slices are weighted based on their proximity to the end of the frame and then added together. For example, in a 7 slice overlap, slice 29 in the first frame will overlap with slice 1 in the second frame. Slice 30 in the first frame will overlap with slice 2 in the second frame, etc. The following equation can be used to calculate the weights:

weight for slice $A$=(relative position of slice $A$)/(relative position slice $A$+relative position of slice $B$)

In the above example, the relative position is the number of slices that a particular slice is located from the end of the frame. For example, slice 2 would have a weight of ⅔ and slice 30 would have a weight of ⅔. Slice 1 would have a weight of ⅛, and slice 29 would have a weight of ⅞. The weights are also calculated with the assumption or approximation that the sensitivity drops off linearly towards the detector edge. Of a pair of corresponding overlapping slices, the one which was acquired closer to the detector center will contribute more signal, and hence it is weighted accordingly.

Referring again to FIG. 7, step 34, if the current frame is not the first frame, then it will typically be overlapped with a portion of the previous frame. Accordingly, the overlapping slices from the previous frame are retrieved.

In step 36, the overlapping slices for the adjacent frame are weighted, as described above, summed, and stored.

In step 38, if the current frame is not the last frame, then typically it will be overlapped with a portion of the next frame. Accordingly, the overlapping slices from the current frame are saved in a designated memory and filename so that they can be retrieved during the processing of the next frame of PET data.

In step 40, after the PET data has been attenuation corrected (step 30), transformed to sinogram format (step 32), and overlapped (steps 34-38), a PET image is generated. The PET image generation based on sinogram format data is performed according to methods well known in the art.

After the PET images are created, they are transferred to the CJM 352, as shown in FIG. 5. The CJM 352 is a server that manages all PET reconstruction requests to the PET image processor 353. It keeps track of all the jobs submitted to the processor queue, their order in the queue, and their time of completion. It may also send reconstruction status notifications to a user interface. The PET images are then stored in the PET database 348.

The CT images and the PET images are subsequently sent to the PET-CT image processor 410 which generates a fused PET-CT image. The fused PET-CT image shows anatomical structures and locations from CT along with the metabolic activity from PET. Exemplary embodiments of the invention can thus provide the advantage of high quality images showing both the structural and functional features of a patient being imaged while providing increased throughput for enhanced efficiency in operation.

While the foregoing specification illustrates and describes the preferred embodiments of this invention, it is to be understood that the invention is not limited to the precise construction disclosed herein. The invention can be embodied in other specific forms without departing from the spirit or essential attributes. Accordingly, reference should be made to the following claims, rather than to the foregoing specification, as indicating the scope of the invention.

What is claimed is:

1. A method for executing a scanning procedure comprising the steps of:
    (a) generating CT image data for a scan;
    (b) generating CT attenuation correction data for the scan;
    (c) acquiring a current frame of PET data for the scan in a 3D format; and
    (d) simultaneously conducting the following steps:
        reconstructing at least a portion of a PET image for the current frame, including
            the step of overlapping a portion of the current frame with an adjacent frame, and
        acquiring at least a portion of a next frame of PET data.

2. The method of claim 1, further comprising repeating step (d) for at least one subsequent frame.

3. The method of claim 1, wherein the 3D format comprises a projection plane format.

4. The method of claim 3, wherein the step of reconstructing at least a portion of a PET image comprises applying a Fourier rebinning process to directly convert the PET data from the projection plane format to a sinogram format.

5. The method of claim 1, wherein the step of overlapping comprises computing a weight for each overlapping slice in the overlapping portion of the current frame and the adjacent frame.

6. The method of claim 1, wherein the adjacent frame comprises a previous frame, and the step of overlapping comprises retrieving a stored overlapping portion of the previous frame.

7. The method of claim 1, further comprising the step of storing an overlapping portion of the current frame to enable overlapping during reconstruction of the next frame.

8. The method of claim 1, further comprising the step of automatically configuring a scan protocol for the PET data based on a scan protocol used to acquire the image CT data.

9. The method of claim 1, further comprising the step of generating a fused PET-CT image with the CT image data and the PET image.

10. The method of claim 1, wherein the reconstructing step includes applying an attenuation correction to the PET image using the CT attenuation correction data.

11. A PET-CT system comprising:
a CT detector;
a PET detector;
at least one memory; and
at least one processor, which is programmed to
control a generation of CT image data for the scan;
control a generation of CT attenuation correction data for the scan;
control an acquisition of a current frame of PET data for the scan in a 3D format; and
control a simultaneous execution of (a) a reconstruction of at least a portion of a PET image for the current frame, including overlapping a portion of the current frame with an adjacent frame, and (b) an acquisition of at least a portion of a next frame of PET data.

12. The PET- CT system of claim 11, wherein the at least one processor is programmed to repeat, for at least one subsequent frame, the step of controlling the simultaneous execution of (a) and (b).

13. The PET-CT system of claim 11, wherein the 3D format comprises a projection plane format.

14. The PET-CT system of claim 13, wherein the reconstruction of at least a portion of a PET image comprises application of a Fourier rebinning process to convert the PET data from the projection plane format to a sinogram format.

15. The PET-CT system of claim 11, wherein the at least one processor is programmed to compute a weight for each overlapping slice in the overlapping portion of the current frame and the adjacent frame.

16. The PET-CT system of claim 11, wherein the adjacent frame comprises a previous frame, and the at least one processor is programmed to retrieve a stored overlapping portion of the previous frame.

17. The PET-CT system of claim 11, wherein the at least one processor is programmed to store an overlapping portion of the current frame to enable overlapping during reconstruction of the next frame.

18. The PET-CT system of claim 11, wherein the at least one processor is programmed to automatically configure a scan protocol for the PET data based on a scan protocol used to acquire the image CT data.

19. The PET-CT system of claim 11, wherein the at least one processor is programmed to generate a fused PET-CT image with the CT image data and the PET image.

20. The method of claim 11, wherein the at least one processor is programmed to apply an attenuation correction to the PET image using the CT attenuation correction data.

* * * * *